United States Patent [19]

Kaufhold

[11] Patent Number: 5,288,932

[45] Date of Patent: Feb. 22, 1994

[54] METHOD FOR THE PRODUCTION OF SUBSTITUTED OR UNSUBSTITUTED CHLOROMETHYL CYCLOPROPANE AND BROMCMETHYL CYCLOPROPANE

[75] Inventor: Manfred Kaufhold, Marl, Fed. Rep. of Germany

[73] Assignee: Huels Aktiengesellschaft, Marl, Fed. Rep. of Germany

[21] Appl. No.: 39,827

[22] Filed: Mar. 30, 1993

[30] Foreign Application Priority Data

Apr. 16, 1992 [DE] Fed. Rep. of Germany ........ 4212766

[51] Int. Cl.$^5$ .............................................. C07C 17/16
[52] U.S. Cl. .................................... 570/186; 570/124; 570/137
[58] Field of Search ........................ 570/137, 124, 186

[56] References Cited

U.S. PATENT DOCUMENTS

| 2,950,328 | 8/1960 | Orchin | 570/186 |
| 2,967,181 | 1/1961 | Herrick et al. | 570/186 |
| 4,012,430 | 3/1977 | Verbrugg et al. | 570/186 |

*Primary Examiner*—Werren B. Lone

*Attorney, Agent, or Firm*—Oblon, Spivak, McClelland, Maier & Neustadt

[57] ABSTRACT

The present invention relates to a method for the production of substituted or unsubstituted chloromethyl and bromomethyl cyclopropane having a degree of purity above 85%, particularly above 90%, by reacting a hydroxymethyl cyclopropane of the formula

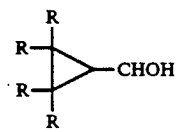

where R is H, or one or two R groups are alkyl of from 1 to 10 carbon atoms or phenyl, with methane sulfonic acid chloride or methane sulfonic acid bromide in the presence of a trialkylamine and, if necessary, an organic solvent, preferably an organic solvent containing oxygen, at a temperature of from $-20°$ C. to $+30°$ C. over a period of time of from 1 to 30 hours, then heating the reaction mixture to a temperature of from $40°$ to $80°$ C., or to reflux temperature, without isolating the intermediate mesylate.

17 Claims, No Drawings

METHOD FOR THE PRODUCTION OF SUBSTITUTED OR UNSUBSTITUTED CHLOROMETHYL CYCLOPROPANE AND BROMOMETHYL CYCLOPROPANE

BACKGROUND OF THE INVENTION

Field of the Invention

The present invention relates to a method for the production of chloromethyl cyclopropane and bromomethyl cyclopropane having the formula (1) shown below, as well as corresponding compounds bearing ring substituents. The present method comprises reacting hydroxymethyl cyclopropane (2) or the corresponding substituted compound with methane sulfonic acid chloride or methane sulfonic acid bromide (referred to as "mesyl chloride" or "mesyl bromide") in the presence of a tertiary alkyl amine in a so-called "single-pot" reaction:

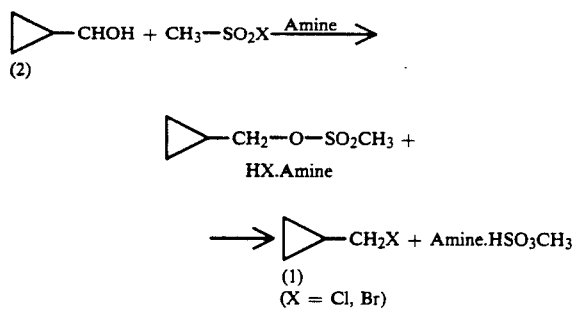

Syntheses of haloalkanes from alcohols, particularly primary haloalkanes having a cyclopropyl group bound thereto, tend to result in isomerization (as shown below). For example, in the reaction of the compound of formula (2) with hydrochloric acid, 4-chlorocyclobutane is obtained in a good yield as the main product:

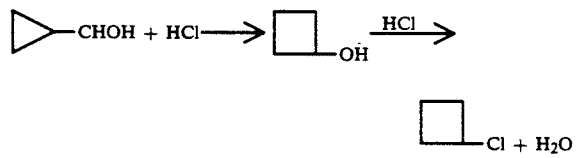

(see Lee, C. C., and Cessna, A. J., *Can. J. Chem.*, vol. 58 (1980) 11, 1075–79).

Special measures are required to avoid such isomerization. To suppress this isomerization, the so-called "tosylate' procedure is recommended in the literature (see *Weygand/Hilgetag*, "Organisch-Chemische Experimentierkunst [The Art of organic Chemistry Experimentation]," 4th edition, 1970, J. Ambrosius Barth, Leipzig, page 232). In contrast to other methods, which lead intermediately via sulfinates or phosphorous acid ester derivatives, the tosylate method requires two steps. First, a toluene sulfonic acid ester (a "tosylate") or a methane sulfonic acid ester (a "mesylate") of the alcohol is produced, and this product is reacted with an alkali metal halide or alkaline earth metal halide in another solvent (e.g., 2-ethoxyethanol or acetone) to provide the alkyl halide product.

The production of the tosylates or mesylates takes place in known manner, by reaction of the alcohols with tosyl chloride or mesyl chloride, in the presence of a strong base, such as pyridine or a pyridine derivative (see the above literature references and the citations therein). For liquid alkyl tosylates and mesylates, post-reaction processing (also referred to as the "work-up") involves ice water washing, extraction and distillation. The pyridine, used in great excess as the solvent, is soluble in water, and thus is completely washed out with water, and is discarded as an aqueous solution. Prior to water washing, the pyridine is sometimes acidified to form an even more water-soluble salt. Processing of this waste water to recover the water-soluble pyridine is very complicated and costly.

The second stage of the tosylate method, reaction of the alkyl tosylate or mesylate with an alkali or alkaline earth halide, also requires a polar, water-soluble solvent. The separation of the polar, water-soluble solvent from the resulting by-product, an alkali or alkaline earth salt of toluene or methane sulfonic acid, is also possible only with very complicated and costly technical measures.

All known tosylate and mesylate methods have a high consumption of chemicals, are technically complicated and time-consuming, and lead to problems in waste disposal. Therefore, a method in which hydroxymethyl cyclopropane is converted to chloromethyl cyclopropane or bromomethyl cyclopropane with mesyl chloride or mesyl bromide which permits easy recovery of the solvents is desirable. There is great interest in such a method, which produces chloromethyl cyclopropane or bromomethyl cyclopropane from hydroxymethyl cyclopropane with little technical effort and without the consumption of environmentally harmful reagents such as pyridine and alcohol glycol ethers. Specifically, such a method which provides chloromethyl cyclopropane or bromomethyl cyclopropane having a purity of more than 85%, preferably more than 90%, is strongly desired because these products are important raw materials for pharmaceutical products.

It has been surprisingly found that in the reaction of a hydroxymethyl cyclopropane with a mesyl halide, the water-soluble pyridine base previously considered necessary can be advantageously replaced with such a trialkylamine, which is either not very soluble or even insoluble in water.

Furthermore, it has been surprisingly found that suitable temperature control and a precisely selected time of mesyl halide addition result in direct formation of chloromethyl cyclopropanes and bromomethyl cyclopropanes in a good yield. That is, the intermediate mesylate does not have to be isolated, but rather, continues to react with the halide present in the reaction mixture to form the target product.

SUMMARY OF THE INVENTION

Accordingly, an object of the present invention is to provide a method for the production of substituted or unsubstituted chloromethyl cyclopropanes and bromomethyl cyclopropanes with a degree of purity above 85%, particularly above 90%, by reacting a hydroxymethyl cyclopropane of the formula

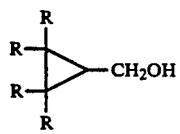

where R is H, or one or two R groups are independently alkyl of from 1 to 10 carbon atoms or phenyl, with methane sulfonic acid chloride or methane sulfonic acid bromide, in the presence of a trialkylamine, and if desired or necessary, an organic solvent, at a temperature of from −20° C. to +30° C. for a length of time of from 1 to 30 hours, then heating the reaction to a temperature of from +40° to 80° C., or to reflux temperature, without isolating the intermediate mesylate.

The present invention contrasts with the method(s) described in the above literature references. Although halogenated compounds can be formed (along with other compounds), the above literature references teach that tosylates or mesylates must first be produced and isolated in order to produce pure halogen-containing compounds. The tosylates or mesylates must then be converted to the halogen-containing compound in a second step with an alkali or alkaline earth halide in a polar solvent which contains oxygen.

One advantage of the present method is the easy recovery of the trialkylamine and, if present, any solvent used, in a surprising manner.

Suitable solvents include organic solvents; for example, hydrocarbons and ethers. Suitable hydrocarbons include n-pentane and n-hexane. However, preferred solvents are those organic solvents containing oxygen, particularly ethers, such as diethyl ether, dipropyl ether, diisopropyl ether and particularly preferably methyl t-butyl ether. The amount of solvent used is from 1 to 10 times by weight of the amount of the alcohol starting material of the formula (2) used, preferably from 1 to 3 times. Most preferably, the solvent is selected to have a boiling point which differs from the boiling point of the desired halomethyl cyclopropane product and from the boiling point of the trialkylamine by at least 5° C., preferably by at least 10° C., and particularly by at least 15° C.

The trialkylamine to be used in the present method can be symmetrical or unsymmetrical, and be used alone or in a mixture. For economic reasons, preferred trialkylamines include short-chain amines available commercially, such as triethylamine, tripropylamine, tri-n-butylamine, triisobutylamine, tripentylamine, tri-hexylamine, triheptylamine, and trioctylamine. Because of its advantageous boiling point and its low solubility in water, tributylamine is particularly preferred. The unsymmetrical trialkylamines which can be used correspond to the general formula $NR_1R_2R_3$, where $R_1$ and $R_2$ independently represent $CH_3$ or $-C_2H_5$ and $R_3=C_3H_7$, and when $R_1$ and $R_2$ are both $CH_3$ or $C_2H_5$, $R_3$ can also represent $-C_4H_9$, $-C_5H_{13}$, $-C_6H_{13}$, $C_7H_{15}$, $C_8H_{17}$, $-C_{10}H_{21}$ or $-C_{12}H_{25}$. Most preferably, the trialkylamine is selected to have a boiling point which differs from the boiling point of the desired halomethyl cyclopropane product by at least 5° C., preferably by at least 10° C., and particularly by at least 15° C.

The present method is conducted, for example, in the following manner: Hydroxymethyl cyclopropane (HMCP), and a trialkylamine (for example, tributylamine), are mixed in a molar ratio of HMCP:trialkylamine of from 1:1 to 1:10, preferably 1:1 to 1:2, and particularly preferably 1:1.1 to 1:1.3. If desired, a solvent (for example, methyl t-butyl ether) is also mixed with the HMCP and trialkylamine. The weight amount of solvent added is from 1 to 10 times, preferably 1 to 3 times, the weight amount of HMCP. The temperature of this mixture is adjusted to a temperature of from −10° C. to +30° C., preferably to −5° C. to 0° C. Over the course of from 1 to 30 hours, mesyl halide is added dropwise to the reaction mixture, and the temperature of the reaction mixture is maintained at a temperature of from −20° C. to +30° C., preferably at −10° C. to +20° C., particularly preferably at −10° C. to 0° C., by cooling. The amount of mesyl halide added is sufficient to result in a molar ratio of HMCP to mesyl halide of from 1:1 to 1:2, preferably 1:1.01 to 1:1.1. The trialkylamine can be present in a solution with HMCP as discussed above or, alternatively, can be mixed with the mesyl chloride and added to the reaction mixture along with the mesyl chloride.

Preferably, in order to obtain a chloromethyl cyclopropane or bromomethyl cyclopropane having a purity of 85% or higher, particularly preferably 90% or higher, the mesyl halide is added to the HMCP by one of the following procedures:

(A) over the course of from 1 to 3 hours at a temperature of from −5° C. to −20° C.;

(B) over the course of from 3 to 10 hours at a temperature of from −5° C. to +5° C.;

(C) over the course of from 10 to 20 hours at a temperature of from +5° C. to 15° C.; or (D) over the course of from 20 to 30 hours at a temperature of from +20° C. to +30° C.

The addition time for the mesyl halide is dependent on the reaction temperature selected, if the goal of 85-90% pure halomethyl cyclopropane is to be achieved. The lower the temperature selected, the faster the mesyl halide can be added. At −10° C., an addition time of 3 h results in a degree of purity of approximately 93%, while at 25° C., the addition time has to be extended to 23 hours in order to achieve this degree of purity.

After addition of the mesyl halide is complete, the reaction mixture is then heated to a temperature of from +40° to +80° C., preferably to the reflux temperature, if the reflux temperature falls in the range of +40° to +80° C. If a reaction temperature below room temperature (18°-27° C.) was selected for addition of mesyl halide, the reaction mixture is preferably brought to room temperature over the course of 1 to 2 hours after addition of the mesyl halide is complete. This is achieved by removing the cooling means. The temperature is then slowly raised to a temperature of 40°-80° C. over the course of 1 to 2 hours, or preferably, until the reflux temperature is reached. Heating at the raised temperature (40°-80° C., or reflux) continues for about two hours, then the reaction mixture is cooled to a temperature of from 0° to 10° C.

Subsequently, the reaction mixture is neutralized or made basic with basic agents, such as soda lye, potash, calcium hydroxide or another metal hydroxide, or with a metal alkoxide, such as sodium methoxide, potassium methoxide, sodium ethoxide, etc. The basic agent can be added in solid form or as a solution, preferably an aqueous solution.

If an aqueous solution of a metal hydroxide is used for neutralization, the mixture separates into two phases.

The aqueous phase is discarded, and the oil phase is processed by distillation.

The product halomethyl cyclopropane is then isolated from the oil phase mixture. Preferably, the product is isolated by distilling the oil phase mixture. Distillation yields the desired chloromethyl cyclopropane or bromomethyl cyclopropane in a yield of 75-80% and in a purity of over 90%. The trialkylamine and, if present, the solvent are recovered as separate fractions.

Other features of the present invention will become apparent in the course of the following descriptions of exemplary embodiments which are given for illustration of the invention, and are not intended to be limiting thereof.

EXAMPLE 1

A glass apparatus consisting of a three-neck flask is equipped with a stirrer, a thermometer, an addition funnel and a reflux condenser. The following starting materials are mixed in the flask and cooled to $-10°$ C. with stirring:

144 g (1.97 mole) hydroxymethyl cyclopropane (98.6%)
411 g (2.2 mole) tributyl amine (99%)
300 g methyl t-butyl ether (solvent)

Mesyl chloride (232 g, 2.0 mole; 99%) is then added dropwise over the course of 3 hours, maintaining the reaction temperature between $-10°$ C. and $-5°$ C., inclusive. Subsequently, the temperature is raised to $-5°$ C. to $+3°$ C. within one hour. Within another one hour, the temperature is raised to 30° C., and then within a half hour to reflux temperature (64° C.). Heating at reflux is continued for two hours, then the reaction mixture is cooled to 10° C. The methane sulfonic acid salt of tributylamine is neutralized with 430 g (2.15 mole) of an aqueous 20% soda lye, which is added to the reaction mixture at 10° C. The resulting phases are then separated. The aqueous phase, 610 g, is discarded, and the oil phase, 865 g, is processed by distillation.

In a boiling range of 83° to 93° C., at normal pressure, 154 g of chloromethyl cyclopropane with a purity of 93% is obtained. The yield is 80.5% of theory, relative to the starting materials.

In a boiling range of 100° to 104° C. at 33 mbar, 388 g of tributylamine with a purity of 99.2% are obtained. The recovered tributylamine can be used again directly. After neutralization of 24 g destillation residue with additional 40 g of an aqueous 25% soda lye, another 10 g tributyl amine are obtained by separating the aqueous and oel phases.

EXAMPLE 2

The apparatus described in Example 1 is used, the starting materials stated there are used, but the mixture is not cooled. Rather, a temperature of 20° C. is maintained, and the mesyl chloride is added dropwise over 9 hours. Using the same further processing as described in Example 1, chloromethyl cyclopropane having a purity of 89% is obtained in a yield 79% of theory, relative to the starting materials.

EXAMPLES 3 AND 4

The apparatus described in Example 1 is used, the starting materials stated there are used, and, as in Example 2, a temperature of 20° C. is maintained. In Example 3, the addition time is 2 hours, and in Example 4, the addition time is 23 hours. Using the same further processing as in Examples 1 and 2, chloromethyl cyclopropane with a purity of 73% and 93%, respectively, is obtained. The yields are approximately 78 and 81% of theory, respectively, relative to the starting materials.

EXAMPLE 5

The apparatus described in Example 1 is used. The following starting materials are mixed in the flask and cooled to $-10°$ C., with stirring:

65 g (0.9 mole) hydroxymethyl cyclopropane (98.6%)
216 g (1.15 mole) tributylamine (99%)
200 g methyl t-butyl ether (solvent)

Mesyl bromide (169 g, 0.9 mole; 85%) is then added dropwise over the course of 2.5 hours, at a temperature of $-10°$ C. to $-5°$ C. Subsequently, the mixture is stirred at $-5°$ C. for one hour, and then, over the course of one hour, the mixture is heated to reflux. After half an hour of boiling at approximately 64° C., the temperature is reduced to 10° C., and the mixture is made alkaline with 215 g of a 20% solution of soda lye.

Separation of the resulting phases yields:

| oil phase | 531 g |
|---|---|
| aqueous phase | 325 g |

Analysis by gas chromatography indicates the following compounds among the oil phase components, along with a number of unknown compounds:

| methyl t-butyl ether | 36.1% |
|---|---|
| bromomethyl cyclopropane | 15.6% |
| tributylamine | 45.0% |

This corresponds to a yield of approximately 68% of theory, relative to the starting materials. The purity of the bromomethyl cyclopropane after processing is 89.0%.

EXAMPLE 6

The apparatus described in Example 1 is used and the starting materials stated there are used, but in this case, instead of 2.2 moles of tributylamine, 2.2 moles of methylbutyloctylamine is used. Repeating the process described in Example 1, chloromethyl cyclopropane having 91% purity is obtained in a yield that is 81% of theory.

EXAMPLE 7

Work is carried out as described in Example 6, but in this case, instead of 2.2 moles of methylbutyloctylamine, 2.2 moles of dimethyldodecylamine is used. Repeating the process described in Example 1, chloromethyl cyclopropane having 93% purity is obtained in a yield that is 78% of theory.

EXAMPLE 8

The apparatus described in Example 1 is used and the products stated there are used, but in this case, instead of hydroxymethyl cyclopropane, 2,2-dimethyl-1-hydroxymethyl cyclopropane is used. After continuing as in Example 1, 2,2-dimethyl-l-chloromethyl cyclopropane having 89% purity is obtained in a yield that is 81% of theory.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. A method for the production of a haloaklane selected from the group consisting of chloromethyl cyclopropane and bromomethyl cyclopropane, comprising the steps of:

reacting a hydroxymethyl cyclopropane of the formula

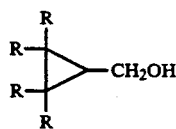

where R is H, or one or two R groups are independently alkyl of from 1 to 10 carbon atoms or phenyl, with a methane sulfonic acid halide selected from the group consisting of methane sulfonic acid chloride and methane sulfonic acid bromide in the presence of a trialkylamine at a temperature of from $-20°$ C. to $+30°$ C. for a length of time of from 1 to 30 hours, to provide a reaction mixture containing an intermediate mesylate, heating said reaction mixture to a temperature of from $+40°$ to $+80°$ C., or to reflux temperature, without isolating said intermediate mesylate, and isolating said haloalkane selected from the group consisting of chloromethyl cyclopropane and said bromomethyl cyclopropane, said haloalkane selected from the group consisting of chloromethyl cyclopropane and bromomethyl cyclopropane having a degree of purity of above 85%.

2. The method of claim 1, wherein said haloalkane selected from the group consisting of chlormoethyl cyclopropane and bromomethyl cyclopropane has a degree of purity above 90%.

3. The method of claim 1, wherein said trialkylamine is selected from the group consisting of triethylamine, tripropylamine, triisobutylamine, tri-n-butylamine, tripentylamine, trihexylamine, triheptylamine, and trioctylamine.

4. The method of claim 1, wherein said trialkylamine has the formula $NR_1R_2R_3$, wherein $R_1$ and $R_2$ independently represents $CH_3$ or $-C_2H_5$ and $R_3=C_3H_7$.

5. The method of claim 1, said hydroxymethyl cyclopropane and said trialkylamine being present in a molar ration of from 1:1 to 1:10.

6. The method of claim 5, said hydroxymethyl cyclopropane and said trialkylamine being present in a molar ratio of from 1:1 to 1:2.

7. The method of claim 6, said hydroxymethyl cyclopropane and said trialkylamine being present in a molar ration of from 1:1.1 to 1:1.3.

8. The method of claim 1, said hydroxymethyl cyclopropane and said mesyl halide being present in a molar ratio of from 1:1 to 1:10.

9. The method of claim 8, said hydroxymethyl cyclopropane and said mesyl halide being present in a molar ratio of from 1:1.01 to 1:1.1.

10. The method of claim 1, said reacting step being conducted in an organic hydrocarbon or ether solvent, said solvent being present in an amount of from 1 to 10 times the amount by weight of said hydroxymethyl cyclopropane.

11. The method of claim 10, wherein said solvent is selected from the group consisting of n-pentane, n-hexane, diethyl ether, dipropyl ether and methyl t-butyl ether.

12. The method of claim 1, wherein said mesyl halide is added by a procedure selected from the group consisting of:

(A) said mesyl halide is added over the course of from 1 to 3 hours at a temperature of from $-5°$ C. to $-20°$ C.;

(B) said mesyl halide is added over the course of from 3 to 10 hours at a temperature of from $-5°$ C. to $+5°$ C.;

(C) said mesyl halide is added over the course of from 10 to 20 hours at a temperature of from $+5°$ C. to $15°$ C.; or (D) said mesyl halide is added over the course of from 20 to 30 hours at a temperature of from $+20°$ C. to $+30°$ C., and said heating step is conducted at reflux temperature.

13. The method of claim 1 further comprising the step of neutralizing said heated reaction mixture.

14. The method of claim 13, wherein said neutralizing step comprises adding an aqueous solution of a basic agent selected from the group consisting of soda lye, potash, metal hydroxides and metal alkoxides to said heated reaction mixture.

15. The method of claim 14, wherein said neutralizing step results in an aqueous phase and an oil phase, and said isolating step comprises separating said aqueous phase from said oil phase and distilling said separated oil phase.

16. The method of claim 4, wherein said trialkylamine has the formula $NR_1R_2R_3$, wherein when $R_1$ and $R_2$ are both $CH_3$, $R_3$ also represents $-C_4H_9$, $-C_5H_{11}$, $-C_6H_{13}$, $-C_7H_{15}$, $-C_8H_{17}$, $-C_{10}H_{21}$ or $-C_{12}H_{25}$.

17. The method of claim 4, wherein said trialkylamine has the formula $NR_1R_2R_3$, wherein when $R_1$ and $R_2$ are both $C_2H_5$, $R_3$ also represents $-C_4H_9$, $-C_5H_{11}$, $-C_6H_{13}$, $-C_7H_{15}$, $-C_8H_{17}$, $-C_{10}H_{21}$ or $-C_{12}H_{25}$.

* * * * *